United States Patent [19]

Vermeer et al.

[11] Patent Number: 5,501,812

[45] Date of Patent: Mar. 26, 1996

[54] TOILET BAR COMPOSITIONS CONTAINING GLYCOLIPID SURFACTANTS AND A PROCESS FOR MANUFACTURING SUCH SURFACTANTS

[75] Inventors: Robert Vermeer, Nutley; Bijan Harichian, South Orange, both of N.J.; John Gormley, Chestnut Ridge, N.Y.; Michael Massaro, Ridgefield Park; George Grudev, Hewitt, both of N.J.

[73] Assignee: Lever Brothers Company, Division of Conopco, Inc., New York, N.Y.

[21] Appl. No.: 135,237

[22] Filed: Oct. 12, 1993

Related U.S. Application Data

[63] Continuation-in-part of Ser. No. 816,421, Dec. 31, 1991, abandoned.

[51] Int. Cl.$^6$ .............................. C11D 1/18; C11D 1/38; C11D 3/26; C11D 7/32
[52] U.S. Cl. .............. 252/174.17; 252/547; 252/DIG. 5; 252/DIG. 6; 252/DIG. 14
[58] Field of Search ................ 252/174.17, DIG. 5, 252/DIG. 6, DIG. 14, 547; 536/18.5, 58

[56] References Cited

U.S. PATENT DOCUMENTS

| | | | |
|---|---|---|---|
| 4,728,455 | 3/1988 | Rerek | 252/99 |
| 4,849,132 | 7/1989 | Fujita et al. | 252/356 |
| 4,943,630 | 7/1990 | Jacquinet et al. | 536/123 |
| 4,959,468 | 9/1990 | Ravi et al. | 536/127 |
| 4,987,223 | 7/1991 | Choay et al. | 536/17.7 |
| 5,032,311 | 7/1991 | Otsuji et al. | 252/174.17 |
| 5,064,555 | 11/1991 | Medcalf, Jr. et al. | 252/121 |
| 5,132,037 | 7/1992 | Greene et al. | 252/108 |
| 5,312,907 | 5/1994 | Schattschneider et al. | 536/18.6 |

FOREIGN PATENT DOCUMENTS

| | | | |
|---|---|---|---|
| 242296 | 10/1987 | European Pat. Off. | A61K 7/50 |
| 0326673 | 6/1988 | European Pat. Off. | C07H 15/04 |
| 499434 | 8/1992 | European Pat. Off. | C11D 17/00 |
| 3803465 | 8/1989 | Germany | C07H 7/033 |
| 56-28296 | 3/1981 | Japan | C11D 1/12 |
| 8901480 | 2/1989 | WIPO | C07H 5/04 |
| 90/09451 | 8/1990 | WIPO | C12P 7/62 |

OTHER PUBLICATIONS

Chemical Abstracts. vol. 101, No. 12, 26 Apr. 1984 Abst. #97490z; Weber, Gerhard; "Uronic Acid for Smoothing Human Skin".

Chemical Abstracts; vol. 111, No. 16, 6 Jan. 1989, Abst. #140226p, Goldstein, "Uronic Acid–Containing Antiwrinkle Cosmetics".

Chemical Abstracts, vol. 86 No. 16, 27 Jan. 1977, Abst. No. 111198r, Koehler, "Use of Uronic Acids as a Substitute for Cortisone in the Production of Drugs and Cosmetics".

European Search Report.

*Primary Examiner*—Asok Pal
*Assistant Examiner*—Patricia L. Hailey
*Attorney, Agent, or Firm*—Ronald A. Koatz

[57] ABSTRACT

The present invention relates to toilet bar soap compositions comprising 1 to 45% by wt. of specified alkali metal (alkyl glycosid) uronates and to processes for making them.

17 Claims, No Drawings

TOILET BAR COMPOSITIONS CONTAINING GLYCOLIPID SURFACTANTS AND A PROCESS FOR MANUFACTURING SUCH SURFACTANTS

This is a continuation-in-part of application Ser. No. 07/816,421, filed on Dec. 31, 1991, now abandoned.

FIELD OF INVENTION

This invention relates to an unexpectedly mild novel toilet bar composition comprising glycolipid surfactants and a new process for preparing such surfactants. The surfactants of the invention are long chained (alkyl glycosid)uronates derived from D-glucuronic acid, D-glucurono-6,3-lactone or D-galacturonic acid.

This invention is also concerned with the preparation of these (alkyl glycosid)uronates having a commercially feasible economical output and with the preparation of these (alkyl glycosid)uronates of high purity and good color. The (alkyl glycosid)uronates are prepared without hydroxyl group protection and without oligomerisation or polymerization.

BACKGROUND OF THE INVENTION

The demand for mild, environmentally friendly surfactants has been steadily rising. In general, most toilet bar compositions contain surfactants based on petro chemicals. Since these materials often have handling, storage and environmental hazards associated with them, it would be most desirable to use surfactants which are instead derived from agriculturally grown materials, such as carbohydrates. These naturally occuring compounds represent a source of renewable raw materials that are readily available, inexpensive, biodegradable, aquatically favorable and optically pure.

(Alkyl glycosid)uronates are known to be prepared by catalytic air oxidation of alkyl glycosides over a platinum or palladium catalyst in alkaline aqueous solution according to the following equation:

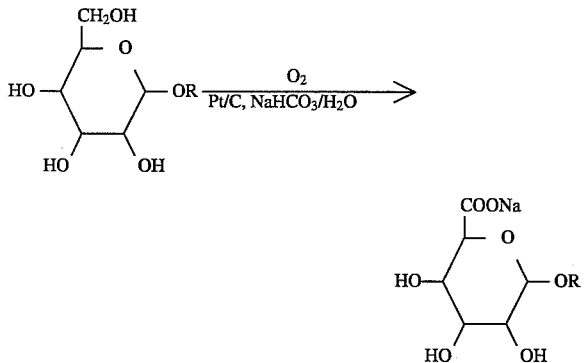

U.S. Pat. No. 2,562,200 to Mehltretter and U.S. Pat. No. 2,845,439 to Corn Products Refining Company, both teach the above identified process using short chained sodium(alkyl glycosid)uronates in which R is methyl, ethyl or hydroxyethyl. European Patent No. 0,326,673 and German Patent No. 3,803,465 to Ripke et al., also teach the above-identified process which is directed towards long chained sodium(alkyl glycosid)uronates in which R is greater than 8 carbons.

These known processes suffer from the distinct disadvantage of being performed under dilute reaction conditions (3 to 6% alkyl glycoside in 85 to 97% water) resulting in low product output and therefore rendering the process uneconomical. In fact, higher concentrations of alkyl glycoside (>10%) cause a retardation of reaction velocity, and yields are diminished (K. Heyms and H. Paulsen, Adv. Carbohyd. Chem., [1962], V. 17, p. 176).

In addition to failing to teach the specific process of the invention, none of these references or other prior art of which applicant is aware of teaches or suggests the use of these surfactants in toilet bar compositions.

More specifically, while Ripke 3,803,465 or EP 0,326,672 suggests that the compounds of the invention may be suited for detergent or cleanser applications, however, there is no suggestion to use them in toilet bar compositions. It must be recalled that the surfactants which are anionic would be classified as generally being harsh to the skin. Thus, while one of ordinary skill in the art might contemplate use of these anionics in detergent compositions where there would be no real direct contact with the skin, such a person would be especially disinclined to formulate the anionic surfactant in a toilet bar where the bar is intimately rubbed by the consumer against the skin. It is only after applicants ran zein tests and discovered the surfactant to be relatively mild on skin that it might even dawn to one of ordinary skill in the art to formulate the surfactant in a bar. Further, the data present in the subject specification cannot be used in making such an assessment.

In the parent of the subject application, the Examiner cited a washing cleanser patent (U.S. Pat. No. 5,132,037) in combination with several chemical abstract references relating to uses of uronic acids. On particular, the Examiner noted CA 101:97490Z, relating to the use of uronic acid for smoothing skin and eliminating flaking. The chemical abstract references, however, all relate to uronic acids, not surfactant derivatives. It is anionic surfactants which are known to be harsh and there would have been no motivation, let alone a teaching, to prepare a surfactant from the acid.

Finally, WO 9302092 to Zschimmer & Schwarz teach galacturonic acid derivatives similar to the compounds of the invention. This application was published after the filing date of the priority date to which the subject application is entitled and is not available as prior art.

Accordingly, it is one object of the invention to provide a novel toilet bar composition comprising the surfactants of the invention.

Another object of the invention is to provide such a bar that is mild to the skin and has good lathering and tactile properties.

It is yet another object of the invention to provide a new and improved process for the manufacture of (alkyl glycosid)uronates, preferably alkali metal (alkyl glycosid)uronates such as sodium(alkyl glycosid)uronates.

It is a particular object of the invention to prepare alkali metal (alkyl glycosid)uronates in good yield, high purity and desirable color within a commercially feasible economical output.

These and other objects of the invention will become more apparent from the detailed description and examples that follow.

SUMMARY OF THE INVENTION

One embodiment of the invention relates to a surprising mild novel bar composition containing glycolipid surfactants, particularly long chained sodium (alkyl glycosid)uronates derived from D-glucuronic acid, D-glucurono-6,3-lactone and D-galacturonic acid.

The second embodiment of the invention relates to a new process for preparing such surfactants. The process is an improvement over the art known process for the preparation of sodium(alkyl glycosid)uronates, wherein the improvement comprises reacting a uronic acid directly or nondirectly with a long chained alcohol in presence of an acid catalyst followed by alkaline hydrolysis containing a bleaching agent. This embodiment of the invention is particularly directed to preparing (alkyl glycosid)uronates, preferably alkali metal (alkyl glycosid)uronates, in good yield, high purity and desirable color within a commercially feasible economical output. The (alkyl glycosid)uronates of the invention have surfactant properties equal to, or better than other well known anionic surfactants based on petrochemicals, thereby indicating that they are viable, environmentally sound alternatives to traditional petrochemical surfactants.

DETAILED DESCRIPTION OF THE INVENTION

The present invention relates to a class of environmentally friendly "green" anionic glycolipid surfactants. In particular, the invention relates to (alkyl glycosid)uronates derived from D-glucuronic acid, D-glucurono-6,3-lactone or D-galacturonic acid.

In one embodiment of the invention, an unexpectedly mild novel toilet bar composition containing sodium(alkyl glycosid)uronate is described.

In a second embodiment of the invention, a new and improved process for the manufacture of (alkyl glycosid)uronates is described.

In general, (alkyl glycosid)uronates are defined as glycosides of uronic acid, uronic acid salts or uronic acid lactones of the following formula:

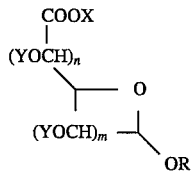

wherein:

n=0–2, preferably 0–1;

m=2–4, preferably 2–3;

Y is a hydrogen atom, mono-, oligo- or polysaccharide; uronic acid, uronic acid salt, uronic acid lactone or polyuronic acid;

R is a straight or branched chain alkyl or alkenyl group which may contain an aromatic, cycloaliphatic or polyalkyloxyalkyl radical comprising 8 or more carbons;

X is a hydrogen atom, alkali metal, alkaline earth metal, ammonium, mono-, di- or trialkanol ammonium group within 2–3 carbon atoms; alkyl-substituted ammonium group with 1–5 carbon atoms; or basic amino acid.

Suitable mono-, oligo- or polysaccharides that may be used to form sodium (alkyl glycosid)uronates of the invention include, but are not limited to glucose, galactose, mannose, gulose, sucrose, lactose, fructose, sorbitol, maltose and starch.

Examples of polyuronic acids, uronic acids or their lactones which may be used to form sodium(alkyl glycosid)uronates of the invention include, but are not limited to D-glucuronic acid, D-glucurono-6,3-lactone and D-galacturonic acid. Other examples include D-mannuronic acid, L-guluronic acid, L-lyxuronic acid, L-lduronic acid, pectin, algin, alginic acid, oxidized starch, oxidized cellulose and acacia.

Suitable aliphatic hydrocarbon radicals include saturated and unsaturated radicals including but not limited to methyl, ethyl, amyl, hexyl, heptyl, nonyl, decyl, undecyl, dodecyl, tridecyl, tetradecyl, pentadecyl, hexadecyl, heptadecyl and octadecyl; allyl, decenyl, dodecenyl, tetradecenyl, oleyl, linoleyl and linolenyl. The active compounds of the invention may contain straight or branched aliphatic groups. Aromatic radicals are exemplified by benzyl, aniline or substituted benzyl or aniline groups. Suitable mixed aliphatic aromatic groups are exemplified by benzylpropyl, phenylethyl, phenoxyethyl and vinylbenzyl. Cycloaliphatic radicals are exemplified by but not limited to cyclopentyl and cyclohexyl.

Suitable alkali metal, alkaline earth metal, ammonium, alkanol ammonium groups include, but are not limited to sodium, potassium, lithium, methylamine, dimethylamine, trimethylamine, ammonia, methylglucamine, glucamine, monoethanolamine, triethanolamine, 2-amino-2-ethyl-1,3-propanediol and chitosamine.

Suitable basic amino acid groups include alkaline salts of glycine, alanine, valine, leucine, serine, lysine, aspartic acid, methionine and glutamine. The (alkyl glycosid)uronates may also be ethoxylated, propoxylated or mixtures thereof.

The chemical behavior of sodium(alkyl glycosid)uronates prepared by the process of the invention results in the formation of pyranosides, furanosides or preferably both.

In one embodiment of the invention, an alkali metal (alkyl glycosid)uronate is used as a surfactant in a toilet bar composition. Examples of specific (alkyl glycosid)uronates are set forth below:

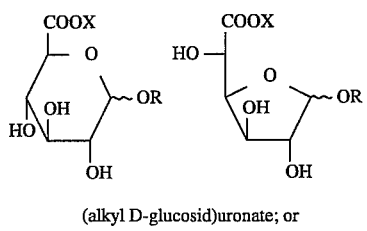

(alkyl D-glucosid)uronate; or

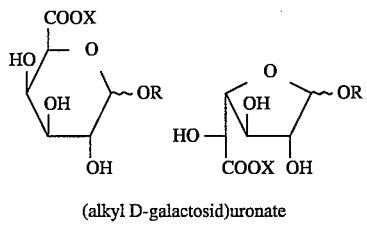

(alkyl D-galactosid)uronate wherein, in each case, R is a substituted or unsubstituted, saturated or unsaturated alkyl group having 8–24 carbons, preferably 10–16 carbons. R may also be an alkoxylated alkyl chain. X may be sodium, potassium, ammonium, alkanolammonium group, or basic amino acid, however sodium is preferred.

In one embodiment of the invention, an unexpectedly mild novel toilet bar composition containing (alkyl glycosid)uronate as the sole surfactant or cosurfactant is described.

Typical toilet bar compositions are those comprising fatty acid soaps used in combination with a detergent and free fatty acids. It should be noted that the composition may comprise no fatty acid soap and may be based on actives other than fatty acid soap. Mildness improving salts, such as alkali metal salt or unsubstituted sodium isethionate, are also typically added. In addition other ingredients, such as germicides, perfumes, colorants, pigments, suds-boosting salts, whiteness and brighteners and anti-mushing agents may also be added.

Fatty acid soaps are typically alkali metal or alkanol ammonium salts of aliphatic alkane or alkene monocarboxylic acids. Sodium, potassium, mono-, di- and triethanol ammonium cations, or combinations thereof, are suitable for purposes of the invention. The soaps are well known alkali metal salts of natural or synthetic aliphatic (alkanoic or alkenoic) acids having about 8 to 22 carbons, preferably 8 to about 18 carbons.

Examples of soap which may be used may be found in U.S. Pat. No. 4,695,395 to Caswell et al., and U.S. Pat. No. 4,260,507 to Barrett et al., both of which are incorporated herein by reference.

In a soap-based bar, fatty acid soaps will generally comprise greater than 25% of the composition, generally from 30–95%. Preferably, the amount of soap will range from 40% to 70% by weight of the composition.

In a detergent bar based on other actives, soap may comprise 0–50% by weight. In general $C_8$–$C_{24}$ fatty acid comprises 5–60% of the composition in such detergent bars.

The detergent bar compositions will also generally comprise a non-soap detergent which is generally chosen from anionic, nonionic, cationic, zwitterionic or amophoteric synthetic detergent materials or mixtures thereof. These surfactants are all well known in the art and are described, for example, in U.S. Pat. Nos. 4,695,395 and 4,260,507 discussed above. One preferred non-soap anionic is a $C_8$–$C_{18}$ alkyl isethionate. These esters may be prepared by the reaction between alkali metal isethionate and mixed aliphatic fatty acids having from 8 to 18 carbons. The alkyl isethionates may be alkoxylated or monoalkoxylated isothionates. The non-soap actives may comprise from 0 to 80% by weight of the composition, preferably 0% to 70% by weight.

A certain amount of free fatty acids of 8 to 18 carbons are also desirably incorporated into soap compositions to act as superfatting agents or as skin feel and creaminess enhancers. If present, the free fatty acids comprise between 1 and 25% of the compositions.

A preferred mildness improving salt which may be added to soap compositions is a simple unsubstituted sodium isethionate. This may be present as 0.1 to 50% of the composition, preferably 0.5% to 0.25%, more preferably 2% to about 15% by weight. Other mildness co-actives which may be used include betain compounds or ether sulfates. These also may be present at 0.1 to 50% of the composition, preferably 0.5% to 25%.

Other optional ingredients which may be present in soap bar compositions are moisturizers such as glycerin, propylene glycol, sorbitol, polyethylene glycol, ethoxylated or methoxylated ether of methyl glycose etc.; water-soluble polymers such as collagens, modified cellulases (such as Polymer Jr®), guar gums and polyacrylates; sequestering agents such as citrate, and emollients such as silicones or mineral oil.

The bar compositions of the invention generally comprise alkali metal (alkyl glycosid)uronate greater than 1%, preferably 1–90%, more preferably 1–60% by weight.

An ideal toilet bar composition is set forth below:

| INGREDIENTS | % BY WEIGHT |
|---|---|
| $C_8$ to $C_{18}$ fatty acid soap | 5–70% |
| (Alkyl glycosid)uronate | 1–60% |
| Non-soap detergent (e.g., $C_8$ to $C_{18}$ alkyl isethionate) | 0–70% |
| $C_8$ to $C_{18}$ free fatty acid | 1–25% |
| Mildness improving coactive | 0.1–50% |
| Moisturizer (e.g., Sorbitol or Glycerin) | 0.1–10% |
| Water soluble polymer (e.g., Cellulose) | 0–10% |
| Sequestering agent (e.g., citrate) | 0.1–0.5% |
| Germicide | 0–0.5% |
| Fragrance or Perfume | 0.1–2.0% |
| Dye stuff (colorants) | <0.1% |
| Suds-boosting salts | 0–5% |
| Optical brighteners | <0.1% |
| Whitening agents | 0.1–0.4% |
| Anti-mushing agents | 0–5% |
| Water | Balance |

In a second embodiment of the invention, a new and improved process for the manufacture of sodium(alkyl glycosid)uronates is described.

It is well known that uronic acids and their lactones undergo many transformations when reacted with alcohols under acidic conditions. The major reactions which are thought to take place for D-glucurono-6,3-lactone and D-galacturonic acid are set forth below:

The Major Reactions of D-Glucurono-6,3-lactone with Alcohols

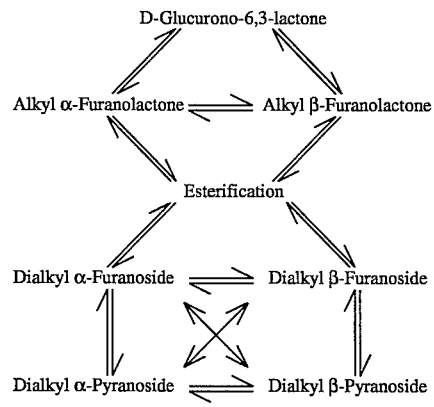

The Major Reactions of D-Galacturonic Acid with Alcohols

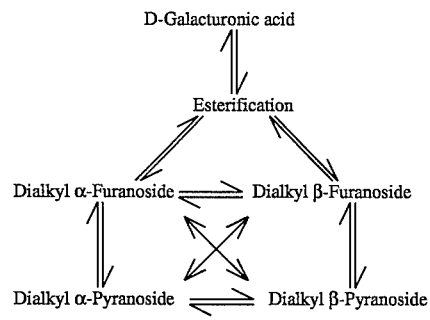

From the above schemes, it can be seen that with uronic acids (or their lactones), glycosidation and esterification are competing reactions resulting in a mixture of anomers. In the case of D-glucurono-6,3-lactone, glycosidation is more rapid than esterification, whereas the reverse holds true for D-galacturonic acid, esterification is more rapid than glycosidation.

It has been found, in accordance with the present invention, that uronic acids or their lactones may be reacted directly or nondirectly with $C_1$–$C_{24}$ alcohols in the presence of an acid catalyst followed by alkaline hydrolysis and optionally containing a bleaching agent.

This aspect of the invention can be more readily understood when reference is made to the general equation:

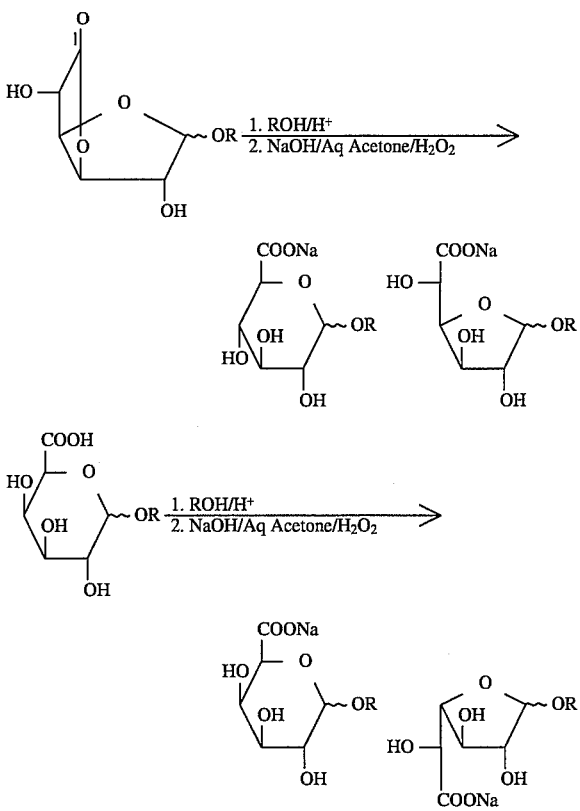

The method of the invention is especially suitable for the manufacture of sodium(alkyl glycoside)uronates where R is an alkyl group having about 8 to 24 carbons, preferably 10–16 carbons. The alcohol may be used in stoichiometric molar amounts with respect to uronic acid or uronolactone. Preferably, however, as seen in Examples 2, 4 and 12, it is added in excess, especially when a low boiling alcohol is used. More preferably, the molar ratio of alcohol to uronic acid or uronolactone is from about 1:1 to 15:1, most preferably 2:1 to 5:1. It is desirable to use water free reaction components, although small amounts of water can be tolerated. Preferably, the water of reaction is removed by simple distillation.

In the process of the invention, the alcohol can be added progressively, but is usually added in full amount at the beginning of the reaction and preferably in excess, but at least in a molar ratio of 2:1 to 10:1, preferably 2:1 to 5:1 with respect to uronic acid or uronolactone used.

The uronic acid or uronolactone used in the method of the invention is preferably in fine powder form, however, crystalline solids, flakes or syrups can be used as well. The reaction is performed at elevated temperature at 60°–180° C., preferably at 70°–95° C.

The reaction can be carried out under reduced pressure, however, it is preferably carried out at normal atmospheric pressure until the uronic acid or uronolactone has completely dissolved, then under reduced pressure to remove the water of reaction and excess alcohol.

When lower boiling alcohols are used, such as for example aliphatic $C_1$ to $C_3$ alcohols, the reaction is preferably performed at the boiling point of the reaction mixture and not greater than 180° C. Higher aliphatic alcohols ($C_{10}$ to $C_{16}$ alcohols) are then added, followed by removal of the lower boiling alcohol and water of reaction by vacuum distillation.

The reactants are reacted with intensive stirring for several hours, e.g., 6 to 16 hours, preferably until the uronic acid or uronolactone has completely dissolved, then for an additional 1 to 8 hours to ensure reaction is complete.

The catalyst used to accelerate the rate of reaction are generally classified as Lewis acids such as $H_2SO_4$, HCl, $HNO_3$, p-toluenesulfonic acid, methanesulfonic acid, sulfonic acid exchange resins and other electron accepting acids, however, sulfonic acid type catalysts are preferred. The catalyst can be added at anytime during the reaction, however, it is preferably added in full amount at the beginning of the invention. The molar ratio of uronic acid or uronolactone to acid catalyst is about 100:1 to 1:1, preferably about 50:1 to 5:1, more preferably about 35:1 to 10:1.

Alkaline hydrolysis of the alkyl(alkyl glycosid)uronate ester to a carboxylate salt may be performed with basic materials such as sodium hydroxide, potassium hydroxide, sodium carbonate, potassium carbonate, ammonium hydroxide, methylamine, ethylamine, triethylamine, glucamine, methyl glucamine, monoethanolamine, diethanolamine, triethanolamine, sodium glycerate, sodium alanate and potassium lysinate among others, however, sodium hydroxide and potassium hydroxide are preferred. The molar ratio of base to the uronate ester of the invention should preferably be 1:1, and in general, an excess of base should be avoided.

Also, hydrolysis may be carried out in water, however, it is preferably carried out in an organic solvent system containing 2–30% water, preferably 3–10%. Typical organic solvents that may be used include, but are not limited to, methanol, ethanol, propanol, isopropanol, acetonitrile, acetone, ethyl ether, dioxane, tetrahydrofuran, chloroform, hexane, toluene and the like, however, acetone is a preferred solvent. Mixtures of solvent can also be used.

Bleaching is sometimes required but not always necessary, since compounds of the invention are of good color. Bleaching agents or peroxy compounds that may be used to further improve color are hydrogen peroxide, sodium perborate, sodium percarbonate, oxone, t-butyl hydroperoxide, benzoyl peroxide, bis(trimethylsilyl)peroxid, peroxyformic acid, peroxyacetic acid, peroxytrifluoroacetic acid, peroxybenzoic acid, m-chloroperoxybenzoic acid, peroxyphthalic acid, peroxymaleic acid, peroxypropionic acid or peroxylauric acid. However, hydrogen peroxide and hydrogen peroxide liberating or generating compounds are preferred. Bleaching may be done in water or inert organic solvent during or after alkaline hydrolysis, preferably, however, bleaching is done during neutralization at 0°–50° C.

Color improvement may also be carried out by using reducing agents belonging to two classes.

The first class of agents comprises compounds which include sulfur in the +4 oxidation state and show a negative oxidation relative to hydrogen. Illustrative of this class are salts of bisulfite, hydrosulfite, metabisulfite, sulfite and mixtures thereof. Suitable salt counter ions include alkali metal, alkaline earth metal, ammonium, alkyl or hydroxyalkylammonium cations and mixtures thereof.

The second class of reducing agents includes those compounds having hydrogen in the −1 oxidation state and show a negative oxidation potential relative to hydrogen. Illustrative of this class are sodium hydride, calcium hydride, sodium aluminum hydride, lithium hydride, sodium borohydride, lithium borohydride, potassium borohydride, diborane, alkyl and alkoxy aluminumhydride, alkyl and alkoxyborohydrides, diimide and mixtures thereof. Particularly preferred among the foregoing are the bisulfite and borohydrides, most especially sodium bisulfite and sodium borohydrides and mixtures thereof. Reduction may be done in water or inert organic solvent during or after hydrolysis, preferably, however, it is done after neutralization at 0°–50° C.

The sodium(alkyl glycosid)uronates prepared by the method of the invention are very pure having a purity range of 90–99%.

Because of their high degree of purity and good surfactant properties, they are well suited for use as biodegradable mild surfactants for detergent, personal product, cosmetic, pharmaceutical and dental applications, particularly personal washing or toilet bar compositions.

Analysis of Sodium(Alkyl Glycosid) uronates by Gas Chromatography

Gas chromatography was found to be a convenient method for the examination of sodium(alkyl glycosid)uronates. The method of persilylation with hexamethyldisilazane (HMDS) and trimethylchlorosilane (TMCS) in pyridine is the simplest way for producing sufficiently stable and volatile derivatives for analysis. The mixture of both agents are more reactive than either reagent alone, and the by-products combine to form neutral ammonium chloride or pyridine hydrochloride.

The purity of several sodium(alkyl glycosid)uronates were determined and found to be 90–99.0%. All products were well separated from starting materials.

Approximately 7–10 mg of sodium(alkyl glycosid)uronate was treated with 1 ml of sil-prep reagent (pyridine:HMDS:TMCS=9:3:1) in a 1 dram stoppered vial containing a magnetic stirring bar. The mixture was stirred vigorously at room temperature for one hour or longer prior to chromatography. The solution became cloudy owing to precipitation of $NH_4Cl$ and pyridine HCl which was filtered through a Cameo II 25 mm filter. From 1–1.1 μl of the resulting mixture was injected into the gas chromatograph.

In order to more fully illustrate the nature of the invention and the manner of practicing the same, the following examples are presented. The examples are not intended to be limiting in any way.

EXAMPLE 1

Prototype-Toilet Bar Composition Containing Sodium(Tetradecyl D-Galactosid)uronate ($SC_{14}$ Gal)

| INGREDIENTS | % BY WEIGHT |
|---|---|
| Sodium Cocoyl Isethionate | 61 |
| Sodium(Tetradecyl D-Galactosid)uronate | 20 |
| Stearic Acid | 13.5 |
| Water | 5 |
| Titanium Dioxide | 0.5 |
| TOTAL | 100 |

Sodium Cocoyl Isethionate (183 g) and Stearic acid (60 g) were melted and mixed in a Brabender at 80° C. Sodium(tetradecyl D-galactosid)uronate (40.5 g), water (15 g), and titanium dioxide (1.5 g) were added and mixed for one hour at 80° C. The ingredients were discharged and pressed into a bar.

No discoloration or decomposition of the uronate occured. In addition, studies suggest that this prototype bar composition is exceptionally mild and has good lathering and tactile properties.

EXAMPLE 2

Preparation Of Sodium(Dodecyl D-Galactosid)uronate ($SC_{12}$Gluc)-Direct Method 10.0 g of D-galacturonic acid monohydrate (0.047 mole), 0.35 g of p-toluenesulfonic acid ($1.84 \times 10^{-3}$ mole) and 18.6 g of dodecanol (0.100 mole) were placed in a three-necked flask equipped with a mechanical stirrer, thermometer and short path distillation head. The mixture was heated at 80°–95° C. until D-galacturonic acid dissolved. A gentle vacuum was applied to remove the water of reaction. The product was cooled to 25° C. and 100ml of acetone and 8 g of 25% aqueous sodium hydroxide solution added followed by stirring overnight to ensure complete hydrolysis. The product was bleached with 1 ml of 30% hydrogen peroxide at 45° C. for three hours, filtered and washed with warm acetone (3×50 ml). Small amounts of dodecanol was removed by soxhlet extraction with acetone and the product dried under vacuum to give 15.5 g of a white crystalline solid in 86% yield.

| GC Analysis (Silylation Method) | |
|---|---|
| Dodecanol | 0.1% |
| p-Toluenesulfonic acid | 0.7% |
| Sodium (Dodecyl β-D-Galactofuranosid)uronate | 33.1% |
| Sodium (Dodecyl α-D-Galactofuranosid)uronate | 5.8% |
| Sodium (Dodecyl α-D-Galactopyranosid)uronate | 50.1% |
| Sodium (Dodecyl β-D-Golactopyranosid)uronate | 10.2% |

| IR Analysis ($cm^{-1}$, Nujol) | |
|---|---|
| OH Stretch | 3400–3100 |
| $CH_2$ Stretch | 2953–2852 |
| C = O Stretch | 1606 |
| $CH_2$ Bend | 1458 |
| $CH_3$ Bend | 1458 and 1377 |
| C—O Stretch | 1090–1022 |

| $C^{13}$ NMR (δ, ppm, $D_2O$/TSP) | |
|---|---|
| —$CO_2Na$ | 177.2–180.5 |
| β-Furanoside Anomeric Carbon | 109.7 |
| β-Pyranoside Anomeric Carbon | 105.0 |
| α-Furanoside Anomeric Carbon | 103.1 |
| α-Pyranoside Anomeric Carbon | 100.7 |
| Sugar Carbons | 71.8–86.8 |
| —O$\underline{CH_2}(CH_2)_nCH_2CH_2CH_3$ | 34.1 |
| —O$CH_2(\underline{CH_2})_nCH_2CH_2CH_3$ | 31.9–32.1 |
| —O$CH_2(CH_2)_n\underline{CH_2}CH_2CH_3$ | 28.6 |
| —O$CH_2(CH_2)_nCH_2\underline{CH_2}CH_3$ | 25.1 |
| —O$CH_2(CH_2)_nCH_2CH_2\underline{CH_3}$ | 16.3 |

| H$^1$ NMR (δ,ppm, D$_2$O/TSP) | |
| --- | --- |
| Anomeric Protons | 5.0 |
| Sugar Protons | 3.3–4.3 |
| —OCH$_2$(CH$_2$)$_n$CH$_3$ | 1.6 |
| —OCH$_2$(CH$_2$)$_n$CH$_3$ | 1.3 |
| —OCH$_2$(CH$_2$)$_n$CH$_3$ | 0.9 |

| Thermospray Mass Spectrometry (60/40 CH$_3$CN/H$_2$O in 0.05M CH$_3$CO$_2$NH$_4$ Buffer) | |
| --- | --- |
| (M + H + H)$^+$ | M/Z = 363 |
| (M + NH$_4$ + H)$^+$ | M/Z = 380 |
| (M + Na + H)$^+$ | M/Z = 385 |
| (M + Na + Na)$^+$ | M/Z = 407 |
| (M + Na + Na$_2$OAC)$^+$ | M/Z = 489 |
| (M + 2CH$_3$CN)$^+$ | M/Z = 543 |

M = 361 (C$_{18}$H$_{37}$O$_7$)

EXAMPLE 3

Preparation of Sodium(Dodecyl D-Glucosid)uronate (SC$_{12}$Gluc) Direct Method

The procedure was similar to Example 2, but the reaction was performed using 10.0 g of D-glucuronic acid (0.052 mole), 0.35 g of p-toluenesulfonic acid (1.84×10$^{-3}$ mole) and 30.5 g of dodecanol (0.16 mole). The yield was 19.6 g (98%).

| IR Analysis (cm$^{-1}$ Nujol) | |
| --- | --- |
| OH Stretch | 3400–3100 |
| CH Stretch | 2953–2852 |
| C = O Stretch | 1600 |
| CH$_2$ Bend | 1458 |
| CH$_3$ Bend | 1458 and 1377 |
| C—O Stretch | 1090–1022 |

| C$^{13}$ NMR (δ ppm, D$_2$O/TSP) | |
| --- | --- |
| —CP$_2$Na | 178.3–180.7 |
| β-Furanoside Anomeric Carbon | 110.4 |
| β-Pyranoside Anomeric Carbon | 105.0 |
| α-Furanoside Anomeric Carbon | 103.0 |
| α-Pyranoside Anomeric Carbon | 101.0 |
| SUGAR CARBONS | |
| —OCH$_2$(CH$_2$)$_n$CH$_2$CH$_2$CH$_3$ | 34.6 |
| —OCH$_2$(CH$_2$)$_n$CH$_2$CH$_2$CH$_3$ | 31.9–32.5 |
| —OCH$_2$(CH$_2$)$_n$CH$_2$CH$_2$CH$_3$ | 28.6 |
| —OCH$_2$(CH$_2$)$_n$CH$_2$CH$_2$CH$_3$ | 25.3 |
| —OCH$_2$(CH$_2$)$_n$CH$_2$CH$_2$CH$_3$ | 16.4 |

| H$^1$NMR (δ ppm, D$_2$O/TSP) | |
| --- | --- |
| Anomeric Protons | 5.0 |
| Sugar Protons | 3.3–4.9 |
| —OCH$_2$(CH$_2$)$_n$CH$_3$ | 1.6 |
| —OCH$_2$(CH$_2$)$_n$CH$_3$ | 1.3 |
| —OCH$_2$(CH$_2$)$_n$CH$_3$ | 0.9 |

EXAMPLE 4

Preparation of Sodium(Tetradecyl D-Glucosid)uronate (SC$_{14}$Gluc) Non-Direct Method 623.4 g of D-glucurono-6,3-lactone (3.54 moles), 26.5 g of p-toluenesulfonic acid (0.14 mole) and 1.3 kg of butanol (17.7 moles) were placed in a three-necked flask equipped with a mechanical stirrer, thermometer and short path distillation head. The mixture was heated at 75°–85° C. until D-galacturonic acid was dissolved. 1.67 kg of tetradecanol (7.80 moles) was then added and a gentle vacuum applied to remove water and butanol. The product was cooled to 25° C., 4000 ml of acetone and 289.5 g of 53% aqueous sodium hydroxide solution added followed by stirring overnight at room temperature to ensure complete hydrolysis. The product was bleached with 25 ml of 30% hydrogen peroxide at 45° C. for 3–5 hours, filtered and washed with warm acetone (3×1500 ml). Remaining tetradecanol was removed by Soxhlet extraction in 500 g batches with acetone or by stirring in warm acetone (10% solids) for three hours followed by filtration, washing and drying giving 841.2 g of a white crystalline solid in 58% yield.

| GC Analysis (Silyation Method) | |
| --- | --- |
| 1-Tetradecanol | 0.2% |
| p-Toluenesulfonic Acid | 1.1% |
| Sodium(Butyl β-D-Glucofuranosid)uronate | 1.2% |
| Sodium(Butyl α-D-Glucofuranosid)uronate | 0.8% |
| Sodium(Butyl α-D-Glucopyranosid)uronate | 3.1% |
| Sodium(Butyl β-D-Glucopyranosid)uronate | 0.8% |
| Sodium(Tetradecyl β-D-Glucofuranosid)uronate | 40.8% |
| Sodium(Tetradecyl α-D-Glucofuranosid)uronate | 10.1% |
| Sodium(Tetradecyl α-D-Glucopyranosid)uronate | 23.5% |
| Sodium(Tetradecyl β-D-Glucopyranosid)uronate | 13.8% |

EXAMPLE 5

Preparation of Sodium(Dodecyl D-Glucosid)uronate (SC$_{12}$Gluc) Non-Direct Method The procedure was similar to Example 4, but the reaction was performed using 10.0 g of D-glucurono-6,3-lactone (0.057 mole), 0.33 g of p-toluenesulfonic acid (1.73×10$^{-3}$ mole), 16.8 g of butanol (0.23 mole) and 31.7 g of dodecanol (0.17 mole). The yield was 13.4 g (61%).

| GC analysis (Silyation Method) | |
| --- | --- |
| Dodecanol | 0.2% |
| p-Toluene sulfonic acid | 0.5% |
| Sodium(Dodecyl β-D-Glucofuranosid)uronate | 47.4% |
| Sodium(Dodecyl α-D-Glucofuranosid)uronate | 15.6% |
| Sodium(Dodecyl α-D-Glucopyranosid)uronate | 26.3% |
| Sodium(Dodecyl β-D-Glucopyranosid)uronate | 9.5% |

EXAMPLE 6

Preparation of Sodium(Decyl D-Glucosid)uronate (SC$_{10}$Gluc) Non-direct Method Prepared according to the procedure described on Example 5 except 26.9 g of decanol (0.17 mole) was used. The yield was 11.8 g (58%).

| GC Analysis (Silylation Method) | |
|---|---|
| Dodecanol | 0.17% |
| p-Toluene sulfonic acid | 0.6% |
| Sodium(Decyl β-D-Glucofuranosid)uronate | 59.3% |
| Sodium(Decyl ∞-D-Glucofuranosid)uronate | 11.8% |
| Sodium(Decyl ∞-D-Glucopyranosid)uronate | 20.5% |
| Sodium(Decyl β-D-Glucopyranosid)uronate | 7.6% |

EXAMPLE 7

Preparation of Sodium(Hexadecyl D-Galactosid)uronate (SC$_{16}$Gluc) Non-Direct Method Prepared according to the procedure described on Example 4 except 10 g of D-galacturonic acid monohydrate (0.047 mole), 20.9 g of butanol (0.28 mole) and 34.2 g of hexadecanol (0.14 mole) were used. The yield was 18.2 g (88%).

EXAMPLE 8

Preparation of Sodium(Tetradecyl D-Galactosid)uronate (SC$_{14}$Gal) Non-Direct Method Prepared according to the procedure described in Example 4 except 750.0 g of D-galacturonic acid monohydrate (3.54 mole) was used. The yield was 1226 g (84%).

| GC Analysis (Silyation Method) | |
|---|---|
| Tetradecanol | 0.2% |
| p-Toluenesulfonic Acid | 1.2% |
| Sodium(Butyl β-D-Galactofuranosid)uronate | 3.5% |
| Sodium(Butyl ∞-D-Galactofuranosid)uronate | 0.7% |
| Sodium(Butyl ∞-D-Galactopyranosid)uronate | 6.2% |
| Sodium(Butyl β-D-Galactopyranosid)uronate | 1.6% |
| Sodium(Tetradecyl β-D-Galactofuranosid)uronate | 27.6% |
| Sodium(Tetradecyl ∞-D-Galactofuranosid)uronate | 7.3% |
| Sodium (Tetradecyl ∞-D-Galactopyranosid) uronate | 41.8% |
| Sodium (Tetradecyl β-D-Galactopyranosid) uronate | 8.9% |

EXAMPLE 9

Preparation of Sodium(Dodecyl D-Galactosid)uronate (SC$_{12}$Gal) Non-Direct Method Prepared according to the procedure described in Example 7 except 26.3 of dodecanol (0.14 mole) was used. The yield was 16.1 g (89%).

| GC Analysis (Silylation Method) | |
|---|---|
| Dodecanol | 0.3% |
| p-Toluene sulfonic acid | 0.6% |
| Sodium(Dodecyl β-D-Galactofuranosid)uronate | 34.5% |
| Sodium(Dodecyl ∞-D-Galactofuranosid)uronate | 4.2% |
| Sodium(Dodecyl ∞-D-Galactopyronosid)uronate | 49.9% |
| Sodium(Dodecyl β-D-Galactopyranosid)uronate | 10.6% |

EXAMPLE 10

Preparation of Sodium(Decyl D-Galactosid) uronate (SC$_{10}$Gal) Non-Direct Method Prepared according to the procedure described in Example 7 except 22.2 g of decanol (0.14 mole) was used. The yield was 12.2 g (73%).

EXAMPLE 11

Preparation of Sodium(Dodecyl Galactosid) uronates Derived From Pectin 5 g of hydrolyzed pectin, 0.17 g of p-toluenesulfonic acid ($8.9 \times 10^{-4}$ mole) and 20 g of dodecanol (0.11 mole) were placed in a three-necked flask equipped with a mechanical stirrer, thermometer and short path distillation head. The mixture was heated at 95°–110° C. for several hours. A gentle vacuum was applied to remove the water of reaction. The product was cooled to 25° C. and 100 ml of 95% aqueous acetone added. The pH of the reaction was adjusted to 9 with 1% sodium hydroxide solution using an automatic titrator. The product was bleached with 1 ml of 30% hydrogenperoxide at 45° C. for four hours, filtered and washed with warm acetone (3×100 ml). Small amounts of dodecanol was removed by Soxhlet extraction with acetone and the product dried under vacuum.

EXAMPLE 12

Preparation of Dodecyl β-D-Glucofuranosiduron-6,3-Lactone 20 g of Glucurono-6,3-lactone (0.11 mole), 0.2 g p-toluenesulfonic acid ($1.05 \times 10^{-3}$ mole) and 164.0 g of dodecanol (0.88 mole) were placed in a three-necked flask equipped with a mechanical stirrer, thermometer and short path distillation head. The mixture was heated to 110° C. until D-glucurono-6,3-lactone dissolved. The reaction mixture was neutralized with 1 ml of 1N methanolic KOH at 25° C., filtered over silica and washed with methanol. A vacuum was applied to remove the methanol and dodecanol yielding a syrup. Hexane was added and dodecyl β-D-glucofuranosidurono-6,3-lactone crystallized selectively. The yield was 15.9 g (42%). The product was recrystallized from hexane/ether mixture. MP 88°–89° C. (99.9% pure).

EXAMPLE 13

Preparation of Sodium(Dodecyl β-D-Glucofuranosid)uronate 5 g of dodecyl β-D-glucofuranosidurono-6,3-lactone (0.015 mole), and 30 ml of water were placed in a one-necked flask. 2 g of 30% sodium hydroxide solution was slowly added and the pH adjust to 8. The aqueous solution was freeze dried giving 5.5 g, 98% yield.

Examples 14–17

SURFACTANT

In order to demonstrate the effectiveness of these compounds as surfactants, various physical properties such as critical micelle concentration, Krafft point, foam height, zein dissolution and detergency were measured. In particular, the properties compared well with some commonly known petrochemically derived anionic surfactants such as sodium dodecyl sulfate (SDS) and sodium dodecanoyl Isethionate (SDI). The results are set forth in Examples 14–18.

EXAMPLE 14

Critical Micelle Concentration (CMC)

The CMC is defined as the concentration at which a surfactant forms micelles in solution. Micellization is the preferred interfacial phenomena, since detergency (solubilization and removal of soils) depends on the formation of these aggregates in solution. Materials that do not form micelles show little or no detergency.

The value of the CMC was determined by using the Wilhemy plate method. While not wishing to be bound by theory, it is believed that surfactants that have low CMC values tend to provide better surfactancy benefits than those with high CMC values.

The CMC values of various surfactants were measured and the results set forth below.

| Critical Micelle Concentration (CMC) of Various Sodium(alkyl D-Galactosid)uronates | |
|---|---|
| SURFACTANT | CMC |
| SDS | 8 mM |
| SDI | 6.2 mM |
| $SC_{10}$ Gal | 1.8 mM ± 0.3 |
| $SC_{12}$ Gal | 0.8 mM ± 0.3 |

Specifically, the CMC was determined by plotting surface tension as a function of log (concentration) and extrapolating linear points to obtain an intersection point. The concentration at this point was taken as the CMC.

As can be seen from the above table, the CMC value for sodium (alkyl D-galactosid)uronates are significantly lower than SDS and SDI. These numbers indicate that these naturally derived surfactants would be expected to have as good or better surfactancy than petroleum derived surfactants, like SDS or SDI.

EXAMPLE 15

Krafft Point

The temperature at which a surfactant begins to form micelles instead of precipitates is referred to as the Krafft Point. At this temperature the solubility of a surfactant becomes equal to its CMC. In general, surfactants with low Krafft Point values are preferred, since these materials offer the advantage of enhanced water solubility and detergency at cold temperatures.

The Krafft point was measured by preparing a 1.0% dispersion of sodium(alkyl glycosid)uronate in water by weight. If the surfactant was soluble at room temperature, the solution was slowly cooled to 0° C. If the surfactant did not precipitate out of solution, the Krafft point was considered to be <0° C. If precipitation occurs during cooling, the temperature at which precipitation occurs was taken as the Krafft point.

If the surfactant was insoluble at room temperature, the dispersion was slowly heated until the solution became homogeneous. At that temperature the Krafft point was taken.

The Krafft point of various sodium(alkyl glycosid)uronates are set forth below:

| Krafft Point (Tk) of Various Sodium(Alkyl Glycosid)uronates | |
|---|---|
| SURFACTANT | KRAFFT POINT (Tk) |
| SDS | 16° C. |
| SDI | 24° C. |
| $SC_{10}$ Gluc | <0° C. |
| $SC_{12}$ Gluc | <0° C. |
| $SC_{14}$ Gluc | <0° C. |
| $SC_{10}$ Gal | <0° C. |
| $SC_{12}$ Gal | <0° C. |
| $SC_{14}$ Gal | <0° C. |
| $SC_{16}$ Gal | 41° C. |

As seen from the above table, the majority of sodium(alkyl glycosid)uronates have favorably low Krafft Points. This finding suggests, that these naturally derived surfactants are highly soluble in water and will exhibit surface activity or micellization at cold temperatures.

EXAMPLE 16

Foam Height

Foam is an important attribute in many consumer products. Foam is one of the dominant factors that determines the commercial value of certain products such as shampoo's, shower gels, personal washing bars and liquid hand soaps. Furthermore, acceptability of many consumer products is closely related to the quality and texture of the foam they produce (physchological aspect).

Since most of the foaming data on surfactants is typically obtained by the Ross-Miles method (G.D. Am. Soc. for Testing Material Method D1173-53 Philadelphia, Pa. (1953); Oil & Soap (1958) 62:1260) the foaming ability of sodium(alkyl glycosid)uronates were measured using this method.

In the Ross-Miles method, 200 mL of a solution of surfactant contained in a pipette of specified dimensions with a 2.9-mm-i.d. orifice is allowed to fall 90 cm onto 50 mL of the same solution contained in a cylindrical vessel maintained at a given temperature by means of a water jacket. The height of the foam produced in the cylindrical vessel is read immediately after all the solution has run out of the pipette and then again after a given amount of time.

Using this method, the foam production (initial foam height in mm) and foam stability (final foam height after 10 minutes in mm) were measured at 0.05% and 0.1% concentration, 40° C. and 0 ppm (parts per million) hardness. The results were set forth below.

| | Ross-Miles Foam Height Assay of Various Sodium(Alkyl Glycosid)uronates after 10 Minutes | | | |
|---|---|---|---|---|
| | 0.05% CONCENTRATION | | 0.10% CONCENTRATION | |
| Surfactant | Initial Foam Height (mm) | Final Foam Height (mm) | Initial Foam Height (mm) | Final Foam Height (mm) |
| SDS | 143 | 128 | 160 | 150 |
| SDI | 130 | negligible | | |
| $SC_{12}$ Gluc | | | 152 | 136 |
| $SC_{14}$ Gluc | | | 162 | 156 |
| $SC_{10}$ Gal | 105 | 99 | 127 | 119 |
| $SC_{12}$ Gal | 126 | 109 | 154 | 142 |
| $SC_{14}$ Gal | 143 | 129 | 161 | 156 |
| $SC_{16}$ Gal | 123 | 119 | 126 | 121 |

As seen from the above table, the foam height of sodium(alkyl glycosid)uronates in most cases are comparable to SDS and SDl. Thus, these anionic sugar based surfactants provide adequate foaming benefits relative to other anionics.

EXAMPLE 17

Zien Solubilization Assay

In vitro "Mildness" Test/Assessing Mildness

It is generally believed that surfactants become irritants because they penetrate the stratum corneum and then react with the inner cells of the epidermis.

Traditionally, the study of percutaneous absorption has focused on measuring the diffusion of chemicals through the stratum corneum.

We have obtained information on mildness potentials of sodium(alkyl glycosid)uronates through the use of in vitro tests which have been demonstrated to correlate well with in vivo tests.

Gotte in Proc. Int. Cong. Surface Active Subs., 4th Brussels [1964],3, 83–90 and Schwinger in Kolloid-Z.Z. Poly., [1969], 233, 898 have shown that a surfactant's ability to solubilize zein, an insoluble maize protein, correlates well with surfactant irritation potential.

More specifically, the greater the zein solubilization, the greater the irritation protential of a surfactant.

In order to test irritancy potential, a 1% solution of surfactant (30 mls) was added to 1.5 g zein and stirred at room temperature for one hour. Residual zein was collected and dried to constant weight. Differences between starting and residual weights were used to calculate % zein dissolved.

Using the zein solubilization assay, the following results were obtained.

| Zoin Solubilization Assay of Various Sodium(Alkyl Glycosid)uronates | |
|---|---|
| SURFACTANT | % ZEIN SOLUBILIZED |
| SDS | 86 |
| SDI | 55 |
| $SC_{10}$ Gluc | 11 |
| $SC_{12}$ Gluc | 22 |
| $SC_{14}$ Gluc | 20 |
| $SC_{10}$ Gal | 9 |
| $SC_{12}$ Gal | 26 |
| $SC_{14}$ Gal | 18 |
| $SC_{16}$ Gal | Insoluble |
| Blank | 9 |

As indicated in the above table, all sodium(alkyl glycosid)uronates unexpectedly solubilize little zein and therefore are mild to the skin, making them especially well suited for personal washing or toilet bar compositions.

EXAMPLE 18

Detergency Evaluation (Oil Soil Removal)

The detergency performance of tetradecyl(D-galactosid)uronate was evaluated on WFK 30D cloth (polyester cloth coated with pigment/sebum) using a tergotometer. The performance of tetradecyl(D-galactosid)uronate was evaluated alone and along with a typical nonionic surfactant (Neodol 25-7 $C_{12}$-$C_{15}$-OH+7EO) at about 0.22 g/L total surfactant. A non-phosphate, zeolite-built burkite base powder was dosed over the side at about 0.75 g/L. The ratio of total surfactant to zeolite burkite base powder was 21.6% to 78.4%. The system was kept at 37° C., pH=10, 120 ppm (parts per million) hardness for 15 minutes. The detergency improvement was measured by a change in reflectance ($\Delta R$) of the stained cloth before and after washing with the detergent prototype. In general, larger reflectance values suggest better detergency and oily soil removal.

| Neodol 25-7:$SC_{14}$Gal | $\Delta R$ |
|---|---|
| 90:10 | 11.8 |
| 75:25 | 12.6 |
| 50:50 | 11.9 |
| 25:75 | 9.2 |
| 0:100 | 6.6 |

The above data suggests at $SC_{14}$ Gal removals oily soil effectively especially when mixed with from about 10% to about 80% of a nonionic surfactant such as Neodol 25-7 which is an alkoxylated surfactant having an average degree of alkoxylation of about 7 and an average chain length of about $C_{12}$ to $C_{15}$.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A toilet bar soap composition comprising about 1 to about 45% by weight of an alkali metal (alkyl glycoside) uronate selected from the group consisting of:

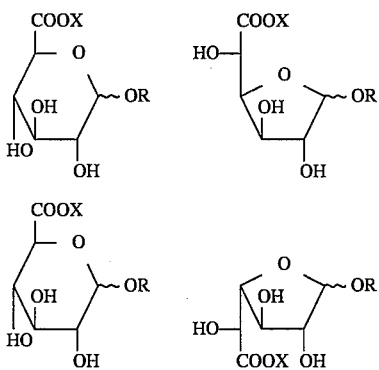

wherein:

R is a substituted or unsubstituted, saturated or unsaturated alkyl group having 8 to 24 carbons; and X is an alkali metal.

2. A soap bar composition according to claim 1, wherein R is 10–16 carbons in chain length.

3. A soap bar composition according to claim 1, wherein the alkyl chain is alkoxylated.

4. A soap bar composition according to claim 1 wherein R is 10–16 carbons and X is sodium.

5. A soap bar composition according to claim 1 comprising:

| INGREDIENTS | % BY WEIGHT |
| --- | --- |
| $C_8$ to $C_{18}$ fatty acid | 5%–70% |
| (alkyl glycosid)uronate | 1%–60% |
| Non-soap Detergent (Alkyl Isethionate) | 0–70% |
| Free Fatty Acid | 1%–25% |
| Moisturizer (e.g., Sorbitol or Glycerin) | 0.1%–10% |
| Cellulase | 0–10% |
| Sequestering agents (e.g., citrate) | 0.1%–0.5% |
| Water and Minors | To Balance |

6. A soap bar composition according to claim 5 comprising:

| INGREDIENTS | % BY WEIGHT |
| --- | --- |
| Stearic Acid | 10–20% |
| Alkali metal (alkyl glycosid)uronate | 15–25% |
| Sodium Alkyl Isethionate | 50–70% |
| Water | 3–10% |
| Titanium Dioxide | 0.1–1% |

7. A process for producing (alkyl glycosid) uronate which process comprises:

(1) adding alcohol to uronic acid or uronolactone such that the molar ratio of alcohol to acid or uronolactone is from about 1:1 to about 10:1 at a temperature of from about 60° to about 180° C. in the presence of a Lewis Acid; and (2) hydrolyzing the resulting alkyl(alkyl glycosid) uronate ester or alkyluronolactone with a basic material.

8. A process according to claim 7, wherein the alcohol is a $C_1$ to $C_{18}$ aliphatic alcohol.

9. A process according to claim 7, wherein the molar ratio of alcohol to uronic acid or uronolactone is 1:1 to 5:1.

10. A process according to claim 7, wherein the temperature is 70°–95° C.

11. A process according to claim 7, wherein the uronic acid or uronolactone is in the form of a fine powder.

12. A process according to claim 7, wherein the reaction is conducted at atmospheric pressure.

13. A process according to claim 7, wherein the Lewis acid is selected from the group consisting of $H_2SO_4$, HCl, $HNO_2$, p-toluenesulfonic acid, methanesulfonic acid and sulfonic acid exchange resins.

14. A process according to claim 7, wherein the basic material is selected from the group consisting of sodium hydroxide, potassium hydroxide, sodium carbonate, potassium carbonate, ammonium hydroxide.

15. A process according to claim 7, wherein hydrolysis is carried out in an inorganic solvent system containing 2–30% water and wherein the solvent is selected from the group consisting of methanol, ethanol, propanol, isopropanol, acetonitrile, acetone, ethyl ether, hexane, toluene and mixtures thereof.

16. A process according to claim 7, which additionally comprises adding a bleaching agent during or after the hydrolysis step and wherein the bleaching agent is selected from the group consisting of hydrogen peroxide, t-butyl hydroperoxide, benzoyl peroxide, oxone, perborate, percarbonate, peroxylauric acid and mixtures thereof.

17. A process according to claim 7, which additionally comprises adding a reducing agent during or after the hydrolysis step wherein the reducing agent is selected from the group consisting of sodium, potassium, aluminum, calcium or lithium salts of bisulfite; hydrosulfite; metabisulfite; sulfite; hydride; borohydride; and mixtures thereof.

* * * * *